United States Patent
Rosati (10) Patent No.: US 10,967,165 B2
(45) Date of Patent: Apr. 6, 2021

(54) SYSTEMS AND METHODS FOR ENHANCING GAS AND VAPOR TRANSFER FOR TISSUE TREATMENT DEVICES

(71) Applicant: Oxyband Technologies, Inc, Mill Valley, CA (US)

(72) Inventor: Coni F Rosati, Carlsbad, CA (US)

(73) Assignee: Oxyband Technologies Inc, St. Louis, MO (US)

(*) Notice: Subject to any disclaimer, the term of this patent is extended or adjusted under 35 U.S.C. 154(b) by 66 days.

(21) Appl. No.: 15/805,921

(22) Filed: Nov. 7, 2017

(65) Prior Publication Data

US 2018/0110969 A1 Apr. 26, 2018

Related U.S. Application Data

(63) Continuation of application No. 11/804,622, filed on May 18, 2007, now Pat. No. 9,808,611.

(60) Provisional application No. 60/872,700, filed on Dec. 4, 2006, provisional application No. 60/872,032, filed on Nov. 29, 2006, provisional application No. 60/833,112, filed on Jul. 24, 2006, provisional application No. 60/801,934, filed on May 19, 2006.

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01)

(58) Field of Classification Search
CPC ...... A61M 37/0015; A61M 2037/0023; A61M 2037/003
USPC ......................................... 604/173
See application file for complete search history.

(56) References Cited

U.S. PATENT DOCUMENTS 6,611,707 B1 * 8/2003 Prausnitz ........... A61B 5/14514
604/21

* cited by examiner

*Primary Examiner* — Phillip A Gray
(74) *Attorney, Agent, or Firm* — Donald R. Boys; Central Coast Patent Agency LLC (57) ABSTRACT

Embodiments of the invention include methods of tissue/wound treatment and associated devices and systems, including devices for breaching bio-films contained in and around wounds, devices for maximizing moisture vapor transmission rate, and tissue dressings with added barrier features for permeable surfaces.

5 Claims, 8 Drawing Sheets

FIG. 7C
Section A-A

FIG. 7D
Section B-B

FIG. 7E
Section B-B

FIG. 8A

FIG. 8B

SYSTEMS AND METHODS FOR ENHANCING GAS AND VAPOR TRANSFER FOR TISSUE TREATMENT DEVICES

CROSS-REFERENCE TO RELATED APPLICATIONS

The present application claims priority to U.S. Provisional Application No. 60/801,934, filed on May 19, 2006; U.S. Provisional Application No, 60/833,112, filed Jul. 24, 2006; U.S. Provisional Application No. 60/872,032, filed Nov. 29, 2006 and U.S. Provisional Application No. 60/872,700, filed Dec. 4, 2006, each disclosure of which is hereby reference in its entirety.

FIELD OF THE INVENTION

Embodiments of the present invention are directed to devices that deliver, transfer and/or maintain gases to a region, and more particularly, to tissue treatment devices.

BACKGROUND OF THE INVENTION

Dressings that deliver therapeutic gas to wounds, can be optimized to address conditions that warrant the need to enhance the penetration of the gases into the tissue, to prevent excess moisture from accumulating at the wound site, and to preserve the gas in the reservoir.

Some wounds can be problematic with limited vascular access from underneath to deliver needed nutrients, repair and infection fighting components to the wounds as well as further localized complications that can limit access for topical treatments such as the development of bio-films, dead tissues and variations in tissue depth, shape and local fluid viscosity.

A subset of wounds consist of collaborative communities or organisms (e.g., anaerobic and aerobic bacteria), where various microbes exist where they would not otherwise be able to but for other microbes. For example, aerobic oxygen consuming microbes can proliferate over a surface allowing oxygen sensitive organisms to thrive underneath where more hypoxic conditions can be established (and to a certain extent encased), allowing anaerobes to flourish. In these cases the biofilms act as a barrier so that such that oxygen or any gas in the environment external to the wound cannot reach the target tissue, fluids or cells passively by diffusion.

Some wounds have dead and decaying tissue covering, surrounding or throughout the wounds which also acts as a barrier so that such that oxygen or any metabolic or therapeutic gas in the environment external to the wound cannot get to the target tissue and cells.

Sometimes wound topography varies considerably, where some portions can have a depth that may be minimally impacted by diffusional process from the surface, limiting any metabolic or therapeutic gas in the environment external to the wound from getting to the target tissue and cells.

Other problems exist in that skin or wounds can over time become a source of excess moisture and moisture vapor. When a film or dressing is placed over the wound or skin, excess moisture must be moved away from the wound to prevent maceration of these tissues. Moisture vapor transmission rate (MVTR) through dressings has been an important feature of wound dressings allowing moisture to essentially evaporate as vapor through thin films, foams and microfibers into the surrounding ambient air. The rate of transmission however is dependent upon the external humidity. The drier the ambient air, the greater the diffusion gradient across the film or dressing, and the higher the MVTR. MVTR may be governed by Fick's Law: $MVTR = K \times \Delta P$.[1] Unfortunately in humid environments the effective MVTR is much lower than that reported in the literature based upon drier laboratory conditions.

[1] http://www.pqri.org/pdfs/whitepaper.pdf

For reservoir based gas delivery devices that provide therapeutic gas to a tissue through permeable, porous or perforated surfaces, there is a potential to lose a fraction of the reservoir contents while removing it from the package and securing it onto or into the target tissue. In this case, there is a need for protecting these surfaces from releasing gases contained within or behind prior to delivery to the target tissue.

SUMMARY OF SOME OF THE EMBODIMENTS

Penetration Enhancement of Gases

Some embodiments of the invention present methods and systems for tissue treatment, especially wound treatment, that include penetrating elements to penetrate the surface of the wound. Such penetrating elements may be included, for example, using a tissue dressing, pre-packaged (preferably) with one or more gases for treating a wound (e.g., oxygen, nitric oxide), examples of which are set forth in Applicant's U.S. Pat. No. 7,014,630 and co-pending U.S. utility patent application Ser. No. 11/356,929, filed Feb. 16, 2006 (the '929 application), both disclosures of which are herein incorporated by reference. Alternatively, such penetrating elements may be part of a separate structure that can be used in conjunction with a tissue dressing or other supply of one or more therapeutic gases.

Accordingly, by adding penetrating elements to some of the embodiments disclosed in the '929 application and the '630 patent, one can produce a tissue/wound treatment device which can penetrate the surface of the wound (e.g., penetrating the bio-film or other dead cells which cuts off the interior of the wound from the environment). For example, such penetrating elements may be established as a bio-film interrupter, including, for example, protrusions that may be sharp like needles or finger-like tentacles, and the like (hereinafter "micropenetrators" or "penetration enhancers") that disrupt the layers of the wound allowing one or more gases from the tissue/wound treatment device access through the layers of the wound, and/or perform as conduits/tubes to enable the delivery of oxygen and/or nitric oxide (for example) to penetrate more effectively.

Maximizing Moisture Vapor Transmission Rate

Some embodiments of the invention present wound dressings are optimized to maximize moisture vapor transmission rate (MVTR) to maintain ideal healing conditions and prevent build up of excess moisture. Accordingly, the present embodiments provide a method to maximize MVTR away from the tissue which is independent of ambient/environmental humidity by maximizing the diffusion gradient by sequestering moisture vapor into a desiccant its unique reservoir. Such tissue dressing embodiments may include conventional desiccant and/or other hygroscopic media such as polyacrylates which have been historically used to absorb body fluids such urine in diapers directly or to dehumidify closed storage containers to preserve moisture sensitive chemicals, or corrosion prone materials. Such embodiments are applicable to tissue/wound dressings, and other skin coverings including masks for cosmetic and aesthetic applications.

Preserving Gas Inside Porous Reservoirs

In tissue dressing embodiments disclosed in the '630 patent and '929 application (as well as FIG. 1 of the present application), some embodiments of the present invention present the use of a second release liner which operates as a temporary barrier to a permeable layer/film provided with the dressing, while the dressing is removed from its package and applied to tissue. Such a release liner enhances the performance of such tissue dressings by preserving gas inside the reservoirs of such dressings prior to its application. Specifically, after removing such dressings from their containers/packaging, the therapeutic gases contained such dressings cannot permeate through the permeable bottom layer of the dressing prior to being placed on a wound. It is only after application of the dressing over the wound, that the permeable film release liner is removed.

Exemplary Aspects of the Above-Noted Embodiments

Accordingly, in one aspect of the invention, a tissue dressing treatment device is provided and includes a reservoir having contained therein one or more predetermined gases at concentrations greater than atmospheric and a plurality of micropenetrators capable of penetrating at least a portion of the tissue and enabling gaseous communication of the one or more gases from the reservoir beyond a surface layer of a target tissue area.

Another exemplary aspect of the invention is directed to a method of treating tissue and includes providing a tissue dressing device comprising a reservoir having contained therein one or more predetermined gases at concentrations greater than atmospheric and a plurality of micropenetrators positioned relative to the reservoir so as to enable gaseous communication of the gases contained in the reservoir through or adjacent to the micropenetrators, affixing the treatment device around a tissue area, and positioning the micropenetrators into the tissue area.

Another exemplary aspect of the invention is directed to a tissue dressing apparatus for supplying one or more predetermined gases to a target area, and includes a top layer, a bottom layer, a reservoir, one or more predetermined gases at concentrations greater than atmospheric contained within the reservoir and a plurality of micropenetrators for enabling gaseous communication below the surface of a target area. The top layer has gas barrier properties and the bottom layer has gas transfer properties, with the top and bottom layers being sealed together to form the reservoir (or being a continuous layer). The tissue dressing apparatus does not generate gas and is packaged prior to use with the one or more predetermined gases.

Another exemplary aspect of the invention is directed to a tissue dressing apparatus for supplying one or more predetermined gases to a target area and includes a top layer, a bottom layer, a reservoir, and one or more predetermined gases at concentrations greater than atmospheric contained within the reservoir. The top layer has gas barrier properties and the bottom layer has gas transfer properties and extends out beyond the top layer at least along a portion of the perimeter of the tissue dressing. The top and bottom layers are sealed together to form the reservoir (or can be a continuous layer), and the tissue dressing apparatus does not generate gas and is packaged prior to use with the one or more predetermined gases.

Another exemplary aspect of the invention is directed to a tissue treatment device which includes a lattice structure to place over a wound, including a first side for facing the target tissue area and a second side for facing away from the target tissue area. The lattice structure includes a plurality of micropenetrators positioned on the first side and traversing from the first side to the second side. The micropenetrators being capable of penetrating at least a portion of the wound and capable of enabling at least communication of gases through or adjacent to the micropenetrators. Upon providing a source of one or more predetermined gases at concentrations greater than atmospheric to the second side of the material, the one or more gases flow through or adjacent to the micropenetrators and into the wound.

Another exemplary aspect of the invention is directed to a method of treating a target tissue area, and includes providing a lattice structure to place over a wound, including a first side for facing a target tissue area and a second side for facing away from the target tissue area, the lattice structure including a plurality of micropenetrators positioned on the first side and traversing from the first side to the second side. The micropenetrators being capable of penetrating at least a portion of wound and capable of enabling at least communication of gases through or adjacent to the micropenetrators. Upon providing a source of one or more predetermined gases at concentrations greater than atmospheric to the second side of the material, the one or more gases flow through or adjacent to the micropenetrators and into the wound. The method may also include providing a supply of one or more gases, applying the lattice structure over the wound, penetrating the target tissue area with the plurality of micropenetrators and enabling gaseous communication between the supply of the one or more gases to the micropenetrators.

Yet another exemplary aspect of the invention is directed to a tissue dressing for maximizing moisture vapor transmission rate (MVTR), and includes a film for covering a target tissue area having sufficient permeability to allow moisture vapor to communicate therethrough, a gas reservoir positioned on a side of the film opposite the target tissue area, and a hygroscopic dessicant material contained within the reservoir. The dessicant material actively absorbs moisture vapor communicating through the film thereby maximizing MVTR in and around the target tissue area.

Yet another exemplary aspect of the invention is directed to a tissue dressing apparatus for supplying one or more predetermined gases to a target area and includes a reservoir, a permeable layer provided on a tissue facing side of the reservoir and for communicating the one or more predetermined gases, and one or more predetermined gases at concentrations greater than atmospheric contained within the reservoir. The tissue dressing apparatus does not generate gas and is packaged prior to use with the one or more predetermined gases and a hygroscopic dessicant material is contained within the reservoir. The dessicant material actively absorbs moisture vapor communicating through the permeable layer to maximize moisture vapor transmission rate in and around a target tissue area.

Yet another exemplary aspect of the invention is directed to a tissue dressing apparatus for supplying one or more predetermined gases to a target area, and includes a top layer, a bottom layer, a reservoir, one or more predetermined gases at concentrations greater than atmospheric contained within the reservoir, and a hygroscopic dessicant material contained within the reservoir. The dessicant material actively absorbs moisture vapor communicating through the permeable layer to maximize moisture vapor transmission rate in and around a target tissue area. The top layer has gas barrier properties, the bottom layer has gas transfer properties, and the top and bottom layers are sealed together to form the reservoir (or be a continuous material), and the tissue dressing apparatus does not generate gas and is packaged prior to use with the one or more predetermined gases.

Yet another exemplary aspect of the invention is directed to a tissue dressing apparatus for supplying one or more predetermined gases to a target area, and includes a reservoir, a permeable layer provided on a tissue facing side of the reservoir and for communicating the one or more predetermined gases, and one or more predetermined gases at concentrations greater than atmospheric contained within the reservoir. The tissue dressing apparatus does not generate gas and is packaged prior to use with the one or more predetermined gases. The apparatus also includes a perimeter adhesive and a perimeter release liner and a permeable layer release liner capable of being released from the permeable layer after a perimeter of the tissue dressing apparatus is adhered to a target area of tissue.

Yet another exemplary aspect of the invention is directed to a tissue treatment device and includes a reservoir having contained therein one or more predetermined gases at concentrations greater than atmospheric, a permeable layer provided on a tissue facing side of the reservoir and for communicating the one or more predetermined gases and a water soluble film provided on the permeable layer that restricts gas transfer.

Yet another exemplary aspect of the invention is directed to a tissue dressing apparatus for supplying one or more predetermined gases to a target area, and includes a reservoir, a permeable layer provided on a tissue facing side of the reservoir and for communicating the one or more predetermined gases, one or more predetermined gases at concentrations greater than atmospheric contained within the reservoir, wherein the tissue dressing apparatus does not generate gas and is packaged prior to use with the one or more predetermined gases, an adhesive to attach the reservoir to the tissue; and a release liner that protects the permeable layer while it is being removed from the adhesive and simultaneously allowing the adhesive to adhered to a target area of tissue.

These and other aspects/embodiments, objects and advantages of the present invention will be even more apparent with reference to the detailed description and corresponding figures (briefly described below).

BRIEF DESCRIPTION OF THE DRAWINGS

The accompanying drawings, which are incorporated in and constitute a part of this specification, illustrate one embodiment of the invention and, together with the description, explain one embodiment of the invention.

DETAILED DESCRIPTION OF THE PREFERRED EMBODIMENTS

Figure 1:
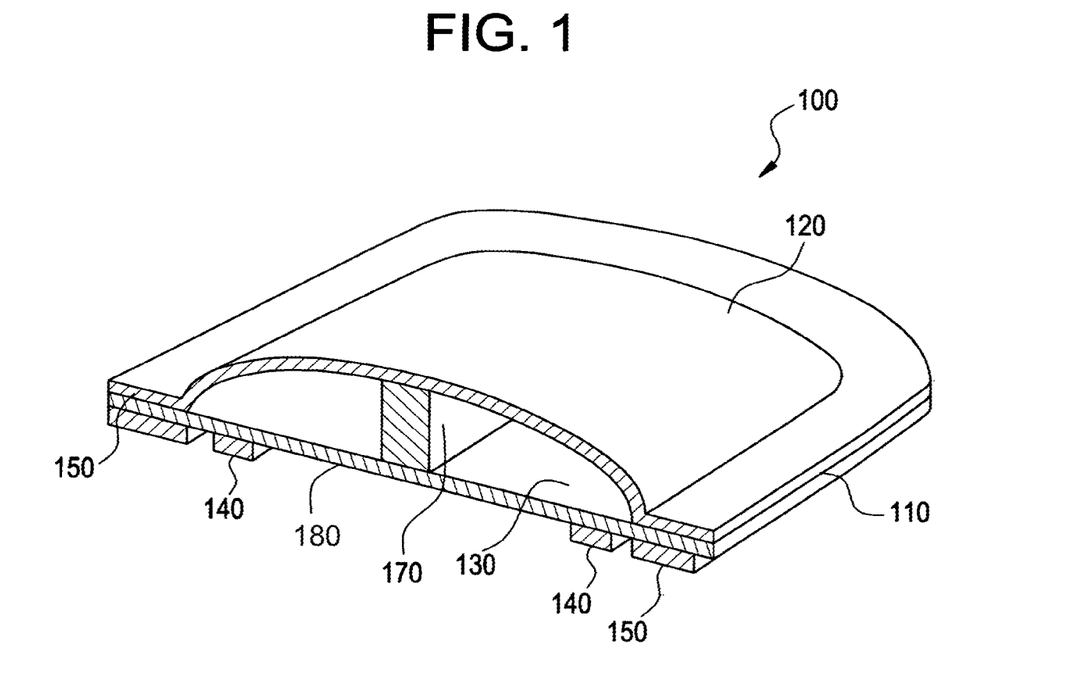
FIG. 1 illustrates one embodiment of a dressing system according to some embodiments of the present invention.

FIG. 1 illustrates an example of one embodiment of the invention of an apparatus for supplying one or more gases to a target area. With reference to use of such an embodiment on biological tissue, this embodiment may be referred to herein as a tissue dressing system 100 (also known as a gas-delivery device). The dressing system 100 is shown as an exemplary perspective cut-away view for clearer understanding. The dressing system 100 may be configured to contain one or more predetermined gases. While any one or more known gases (or volatiles) may be used, the gases included with the dressing system 100 may particularly include oxygen, carbon dioxide, nitrogen and nitric oxide, and combinations thereof. The dressing system can also be used to supply gases to any target areas that would benefit from a locally controlled gas supply such as containers in which it is desired to retard, accelerate, or maintain biochemical reactions, sustain, accelerate, and/or suppress chemical reactions, corrosion, or inhibit the growth or kill organisms, The dressing system 100 may include a seal 110, an external barrier (or top layer) 120, a reservoir 130, an absorbent ring 140, an adhesive backing 150, a permeable film (or bottom layer) 180, and may also include a compliant porous insert 170. As shown, the reservoir may be formed between the upper and lower layers (e.g., being hermetically sealed around the perimeter), but may also be a separate element to the dressing system, or contained within a continuous layer. To that end, in one embodiment, the seal 110 is configured to bond the external barrier 120 and the permeable film 180 together such that the reservoir 130 is formed.

The external barrier 120 is preferably selected to have barrier properties that allow the therapeutic gases to be contained over the duration of use of the dressing. For example, the external barrier 120 may be constructed of metallized polyester, ceramic coated polyester, polyvinylidene chloride laminates such as Saranex®, EVOH laminates such as Oxyshield®, or polyamide laminates such as Capran®. In one embodiment, the external barrier 120 may be configured to conduct heat or electrical stimulation from an external source to the user. In another embodiment for example, polyethylene or another infrared transmittable material may be utilized as the external barrier 120.

The permeable film 180 is preferably configured to be permeable or porous to gases. For example, the permeable film 180 may be constructed of polyurethane, silicone, polyvinylchloride, polyolefins, ethylene vinyl alcohol (EVA) or EVA/polyethylene.

The reservoir 130 is configured to store a gas while the dressing system 100 is worn by a user. In one embodiment, the stored gas within the reservoir 130 is controllably released to the user through the permeable film 180. The amount of gas released to the user while wearing the dressing system 100 may vary according to the concentration of the gas contained within the reservoir 130 and the material properties of the permeable film 180. Other factors such as temperature may also affect the amount of gas released to the user.

The absorbent ring 140 may be located under to the permeable film 180 and may be configured to wick away moisture from the wound or skin surface. In addition, the adhesive backing 150 is configured to adhere the dressing system 100 to the user. Further, the adhesive backing 150 may also be utilized to prevent the gas that is delivered through the permeable film 180 to the wound from escaping. In one embodiment, the adhesive backing 150 may cover the perimeter of the dressing system 100. In another embodiment, the adhesive backing may cover the entire dressing system 100 and may be integrated with the permeable film 180.

Examples of the types of adhesive that may be used in the present invention are described in U.S. Pat. Nos. 6,284,941 and 5,308,887. In one embodiment, the adhesive backing may be comprised of adhesive used in commercially available adhesive bandages. In another embodiment, the adhesive backing may be comprised of a gel adhesive. The gel adhesive may be comprised of a hydrogel. The gel adhesive may also be reusable, such that the dressing system could be removed from the user and replaced more than once. Examples of gels that may be used are described in U.S. Pat. Nos. 4,839,345, 5,354,790 and 5,583,114.

The compliant porous insert 170 is configured to prevent gas debt in areas caused by pressing the external barrier 120 directly on to the permeable film 180. In one embodiment, the compliant porous insert 170 placed within the reservoir 130 and between the external barrier 120 and the permeable film 180.

The proportions of gas-delivery device according to embodiments of the present invention (e.g., dressing system 100) may be influenced by the diffusion rates of the relevant gases through the permeable portion (e.g., film 180), the target gas concentration range (e.g., on the user), and the length of time the gas delivery device is used (e.g., the length of time the dressing system 100 may be worn), If the gas-delivery device includes a seal, then the proportions of the device may be also influenced by the seal integrity between the dressing system 100 and the user.

It is worth noting that some embodiments of the present invention include gas infused devices having controlled and/or customized gas diffusion rates. Specifically, such embodiments may include pre-determined diffusion rates which may be determined by controlling the type of membrane being used, the size and/or amount of pores and/or erosion areas.

In some embodiments, in addition to providing gas to a target area, the gas-delivery device may be configured to deliver biologically beneficial agents such as drugs, minerals, nutrition, amino acids, pH modifiers, anti-microbials (e.g., antibacterials and antifungals), growth factors, and enzymes to the user. In one embodiment, integrating the delivery systems of the gas with the beneficial agent additives may lead to synergistic effects that are not achieved by just the gas or the beneficial agent additives alone. In one embodiment, these biologically beneficial agents may be delivered as microencapsulated agents incorporated in the adhesive backing 150 that could cover the entire or any portion of the permeable film 180. In another embodiment, the microencapsulated agents may be available in a gel matrix in the dressing cavity 180, accessible to the wound through pores or perforations, or using conventional transdermal technologies.

In some embodiments, the gas delivery device includes integrally or as a separate component means to mechanically disrupt the surface of the wound allowing oxygen or other gases to move from the reservoir either directly or through a series of hollow micro-needles or other micropenetrators into the depths of the wound fluid or tissues. By mechanically penetrating passed diffusion barriers caused by bio-films, dead cells or deep irregular wound topography, oxygen (for example) can be delivered and utilized deeper into the wound bed.

Accordingly, as shown in FIGS. 2-6B, a plurality of micropenetrators may be included with tissue dressings (e.g., described above with reference to FIG. 1). Such micropenetrators are advantageous as they can enhance delivery of a therapeutic gas contained in the reservoir of a tissue dressing to breach any occlusions created by living or dead cells or other bio-films established by the body over the wound. Examples of such micropenetrators which could be used with the tissue dressing shown in FIG. 1 can be found with reference to U.S. Pat. Nos. 3,964,482, 5,964,729, 6,780,171, 6,503,231, 7,108,681, and 6,780,171, each disclosure of which is herein incorporated by reference. Generally, these patents disclose use of such penetrators to bypass the skin barrier and deliver drugs using a drug delivery patch. The embodiments according to the present invention are not for the purpose of bypassing or penetrating the skin or stratum corneum.

In some embodiments of the present invention, such micropenetrators may be used as an expanded porous film having elongated pores. Such elongated pores may include different lengths depending on the type of wound being treated, or be self adjusting or elongating to accommodate different depths.

In some embodiments, bio-film micropenetrators may in themselves be beneficial to the wound. Specifically, bioactive materials could be used as mechanically abrasive to disrupt a bio-film to allow one or more gases to be delivered deeper. For example, bioactive glass/ceramics/sol gels disclosed in U.S. Pat. No. 6,428,800 may be manufactured to be sharp/penetrating/abrasive for the purpose of disrupting, while also providing the additional bio-beneficial, wound healing and antimicrobial benefits as described in U.S. Pat. No. 6,756,060, and U.S. patent application publication nos. 2004/0151745 and 2004/0166172. For example, particulate bioactive glasses can be used which typically have the following composition by weight percentage: $SiO_2$ 40-60, CaO 10-30, $Na_2O$ 10-35, $P_2O_5$ 2-8, $CaF_2$ 0-25, $B_2O_3$ 0-10, $K_2O$ 0-8, and MgO 0-5. A preferred composition of the bioactive glass is: $SiO_2$ 45, CaO 24.5, $Na_2O$ 24.5, and $P_2O_5$ 6. A preferred particle size range for the bioactive glass to be practical as an abrasive is in the range of 10-90 microns.

While the above-described embodiments are particularly useful when combined with the tissue/wound treatment reservoir-based devices disclosed in FIG. 1 (and the '929 application and '630 patent), some embodiments of the present invention may also be useful in oxygen generating devices (e.g., using hydrogen peroxide and/or other electrical, biological, chemical and/or electro-chemical devices). Positive pressure generated from such devices may be used advantageously to move gas into the tissue/wound.

Further embodiments with regard to micropenetrators, may include a tissue dressing having a positive displacement mechanism (e.g., a squeeze bulb) to provide a positive pressure to transfer a bolus of gas into wound cavity. An example of such an embodiment can be found in FIGS. 6A and 6B.

Figure 2:
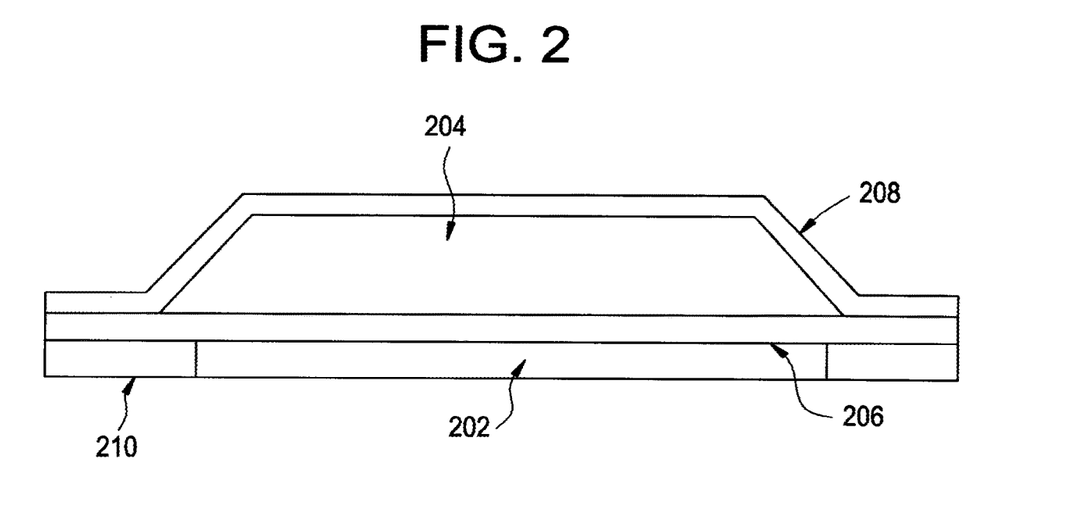
FIG. 2 illustrates a side, cross-sectional view of a tissue/wound dressing device according to some embodiments of the present invention.

Accordingly, FIG. 2 illustrates a side, cross-sectional view of a tissue/wound dressing device according to some embodiments of the present invention, which includes plurality of micropenetrators 202 (e.g., penetration enhancers). As shown, the device may include a gas reservoir 204 (e.g., oxygen, nitric oxide), a porous or otherwise permeable film 206, a barrier area 208 and adhesive 210.

In general, the micropenetrators may be flexible or rigid, and can be made of various materials including plastic, metal, bio-active mineral/glass, and the like.

Figure 3:
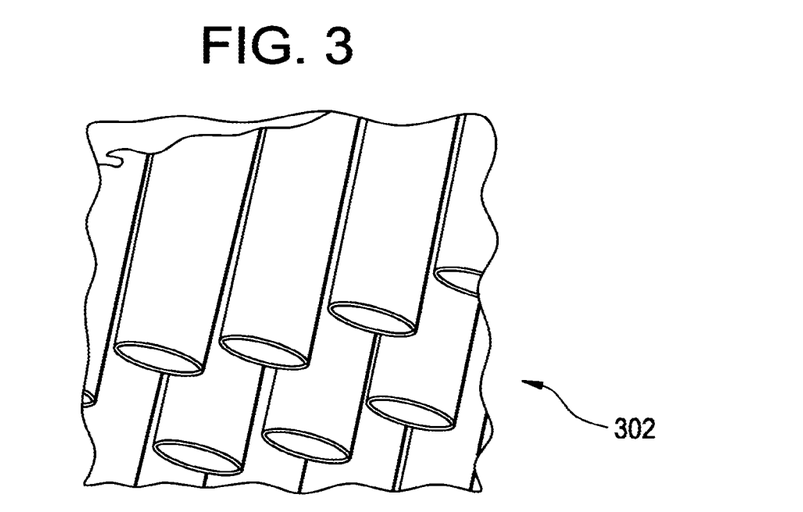
FIG. 3 is a perspective, enlarged view of an example of a plurality of micropenetraters, comprising a plurality of tubes, according to some embodiments of the invention.

FIG. 3 is a perspective, enlarged view of an example of a plurality of micropenetraters, comprising a plurality of tubes 302, which may be polymer, ceramic and/or metal based. Such tubes may be affixed through the permeable film 206 (or an anchoring film used in place of the permeable film) shown in FIG. 2, or provided on a separate member which may be affixed to the permeable film without piercing through the film. Such attachment may allow one end of the micropenetrators to pierce the permeable/anchoring film upon use of the tissue dressing.

Figure 4:
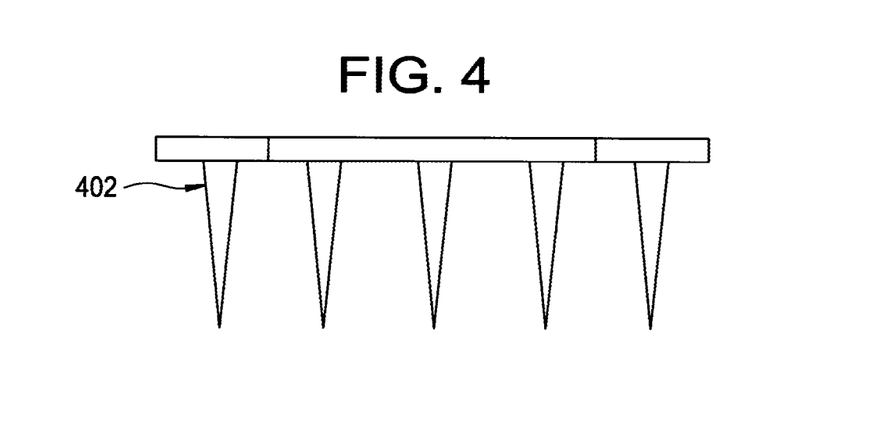
FIG. 4 is a side, enlarged view of another example of a plurality of needle-like micropenetrators, according to some embodiments of the invention.

FIG. 4 is a side, enlarged view of another example of a plurality of micropenetrators 401. In this example, each micropenetrators may comprise a needle-like penetrator, which may be solid, or hollow, the later of which may include one or more openings to allow gaseous communication.

Figure 5A:
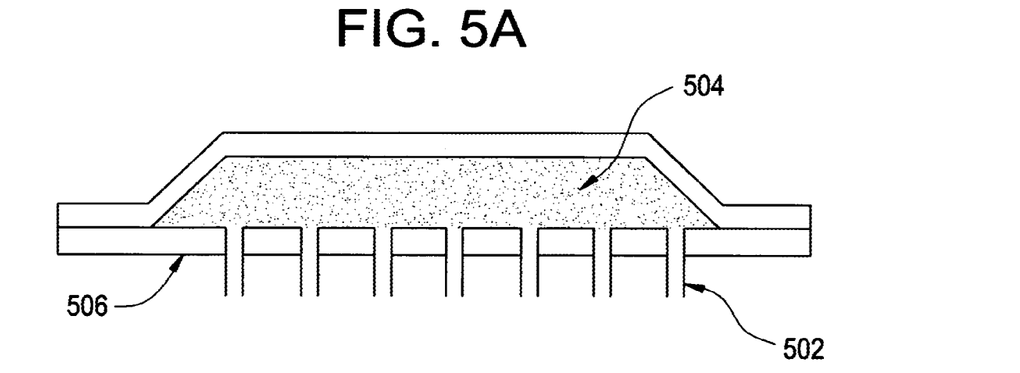
FIG. 5A illustrates a side, cross-sectional view of a tissue dressing having micropenetrators according to some embodiments of the present invention.

FIG. 5A illustrates a side, cross-sectional view of an embodiment of the present invention illustrating the use of micropenetrators 502 (enlarged for illustrative purposes), which may be on the exterior of the reservoir 504, protrude from the porous film 506, or protrude through an anchoring film used in place of the permeable film.

Figure 4A:
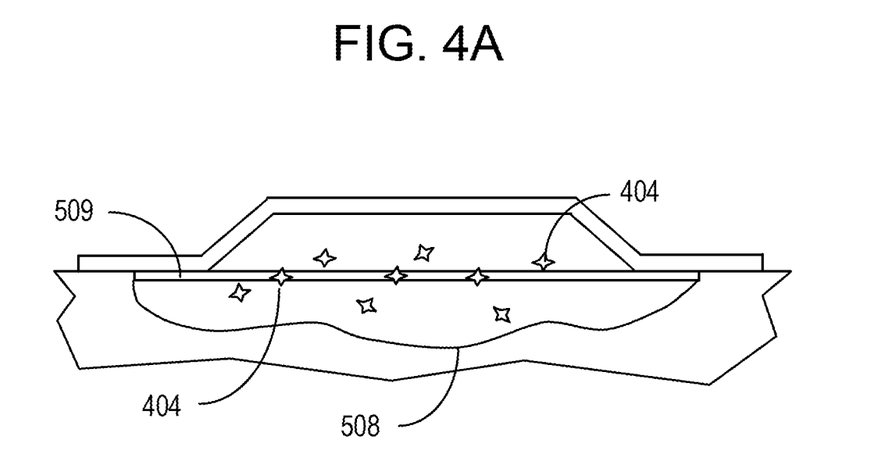
FIG. 4A is a side, enlarged view of another example of a plurality of particle-like micropenetrators, according to some embodiments of the invention.
Figure 5B:
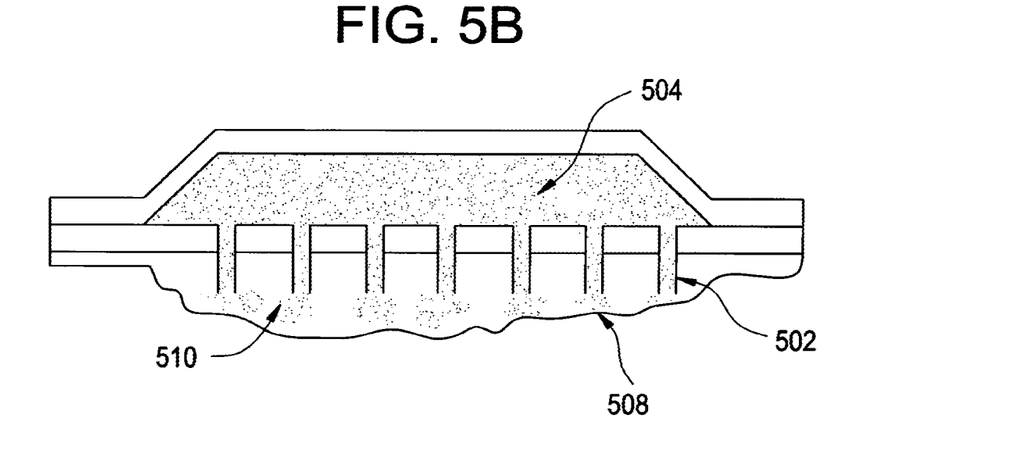
FIG. 5B illustrates a side, cross-sectional view of a tissue dressing having micropenetrators according to some embodiments of the present invention being used in conjunction with a wound.

FIG. 5B illustrates the side, cross-sectional view of FIG. 4A, with the device placed over a wound 508, and a gas 510 flowing into the wound.

Figure 6A:
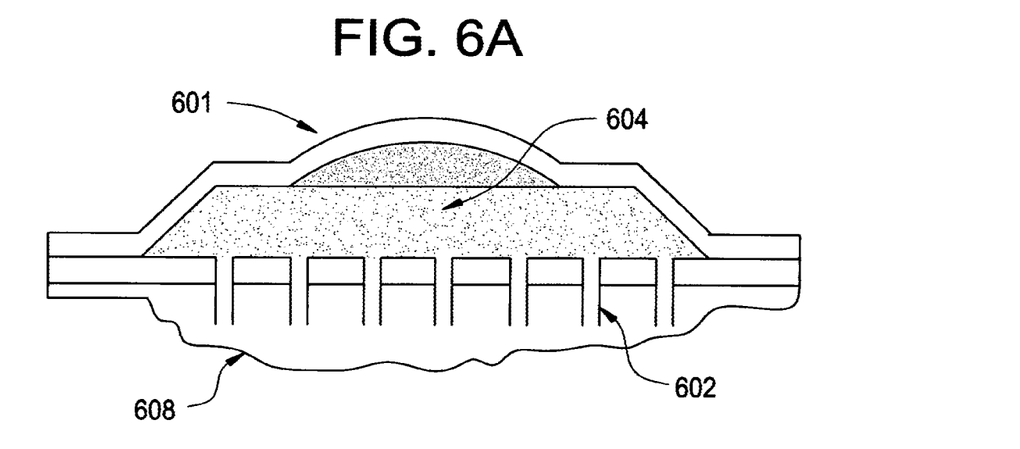
FIG. 6A illustrates a side, cross-sectional view of a tissue dressing having micropenetrators and a cavity for enhancing gas delivery, prior to activation, according to some embodiments of the present invention.
Figure 6B:
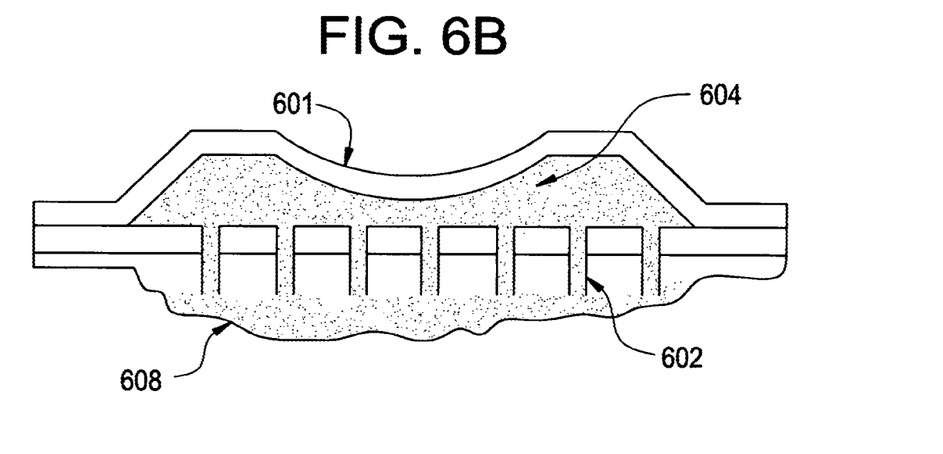
FIG. 6B illustrates a side, cross-sectional view of a tissue dressing having micropenetrators and a cavity for enhancing gas delivery, after activation, according to some embodiments of the present invention.

FIGS. 6A and 6B illustrate a positive pressure displacement device, a squeeze bulb 601, which may be a thermo formed cavity (though an external device/squeeze bulb may also be used which is in communication with the reservoir. Such a squeeze bulb may act as a force-activated bi-stable dome that upon pressing, can "snap" irreversibly down (see FIG. 6B), expelling a gas volume inside the dome (e.g., twice the volume of the cavity of the bulb). The gas may be expelled through the micropenetrators 602 and into the wound 608.

In some embodiments of the present invention, an installation tool may be used to facilitate the processing of disrupting bio-films, tissues or wounds. Such tools are known, being currently used for transdermal, drug-delivery patches. Such tools may be used to effectively create breaches through tissues/wounds, and then the tissue/wound dressing with may be applied to the tissue/wound.

Maximizing Moisture Vapor Transmission Rate (MVTR)

State of the art wound dressings and other products such as diapers today incorporate absorbent materials to wick away and use high MVTR materials to allow moisture vapor to evaporate away from the surface of wounds and skin. Some embodiments of the present invention present reservoir based wound dressings which are optimized to maximize moisture vapor transmission rate (MVTR) away from the wound to maintain moist healing and prevent build up of excess moisture.

MVTR for a film, material or dressing is characterized under constant conditions, and is typically governed by thickness and material properties (K), Moisture vapor transmission or diffusion rates are also proportional to the diffusion gradient ($\Delta P$), which is dependent on the level of moisture vapor on both sides. The drier the ambient air, the greater the diffusion gradient across the film or dressing, and the higher the MVTR. MVTR may be governed by Fick's Law: $MVTR = K \times \Delta P$.[2]

[2] http://www.pqri.org/pdfs/whitepaper.pdf

When a film or dressing is placed over the wound or skin, ambient air on the outside varies in humidity. Thus when the wound is exuding high levels of moisture and the environmental humidity in non-laboratory conditions is high, the effective MVTR across the dressing in use on a patient can be zero because there is no diffusion gradient when the ambient air outside the dressing is saturated in high humidity.

Accordingly, in some embodiments of the invention such as in FIG. 1 or 2, which is illustrated as a tissue/wound dressing but can be used in a form applicable to other skin coverings (e.g., masks), hygroscopic or dessicant materials that absorb moisture and moisture vapor can be included in the reservoir which contains the one or more therapeutic gases. Ideally these materials would be the same or similar to materials used currently to dehumidify closed containers such as silica gel, polyacrylates or bentonite clay. However, in this invention, the dessicants are not being used prevent the corrosion or chemical breakdown of materials and drugs, but rather is being uniquely used to maximize the moisture vapor diffusion gradient away from the wound, across the permeable film side of the reservoir, so as to make the MVTR independent from ambient environmental humidity. One embodiment would bind the dessicant material in the reservoir to all surfaces in the reservoir excluding the permeable surface, so as to maximize the permeable film surface area, and therefore further maximizing the moisture vapor transfer rate by maximizing the area of transfer.

Thus, according to some embodiments for this invention, moisture vapor transmission rates may be maximized by sequestering away vapor as it moves away from the wound by creating a controlled dehumidifying space over the moisture source, the skin and the wound. To that end, some embodiments of the present invention include methods and systems which sequester moisture vapor to maximize MVTR, specifically by maximizing the diffusion gradient for moisture vapor. Since some materials can absorb up to 1000 times their weight in moisture, a relatively small amount of hygroscopic material can absorb a large amount of moisture.

For example, in one embodiment, a reservoir based dressing (e.g., see FIG. 1) maximizes MVTR by using a desiccant in a reservoir, which consists of (for example): a film 180 covering a wound having sufficient permeability to allow moisture vapor to pass through such as polyurethane; a second, barrier type film 120 sealed along an edge of the first film creating a gas reservoir in between; and a hygroscopic dessicant material such as powders or films made of polyacrylates placed in the reservoir to actively absorb moisture vapor that moves into the cavity.

By making component the permeable film highly permeable to moisture vapor, e.g., 1000-4000 gm/m$^2$/day, and making a barrier film with lower MVTR, a system may be created which operates independently from the atmospheric conditions that limit the effective in-use MVTR of current dressings. The dessicant material may be a material such as such as polyacrylate powder, fibers and beads, silca gel, Bentonite clay, sodium, potassium, or calcium crystalline hydrated aluminosilicates, synthetic dessicants.

The above described MVTR embodiments may be used with the tissue dressing apparatuses disclosed herein or in Applicant's U.S. Pat. No. 7,014,630 and co-pending U.S. utility patent application Ser. No. 11/356,929, filed Feb. 16, 2006 (the '929 application).

Preserving Gas Inside Porous Reservoirs

In order to insure that the gases contained in the reservoir of various tissue dressing embodiments according to the present invention (e.g., see FIG. 1), the porous/permeable surface may be covered with a release liner that is removed as a pull tab after the dressing is placed on a target area intended to receive the gas delivery. Specifically, according to the present embodiment, a tissue dressing as described with reference to FIG. 1 (or the '630 patent and/or '929 application) preferably includes two (2) release liners: a perimeter release liner 702 covering and protecting the adhesive around the perimeter of the tissue dressing, and a permeable layer-pull tab release liner 704 covering the perforations that communicate with the reservoir to cover and protect the adhesive as well as block gas transmission from the reservoir to the atmosphere during handling. In another embodiment, the pull tab release liner is provided adjacent an absorbent media which is provided between the release liner and the perforations of the tissue dressing that communicate with the reservoir (preferably, the media is attached thereto). Such absorbent media may include polyurethane foam, gauze, hydrocellular foam, alginates, hydrogel, and hydrocolloids (for example).

In some embodiments of the invention, the perimeter and permeable layer release liners may be incorporated into a single release liner, which is pulled off via one or more pull tabs.

The use of the permeable barrier release liner operates as a temporary barrier while the dressing is removed from its package and applied to tissue enhances the gas delivery performance of tissue dressings. Thus, when using such a tissue dressing, the tissue dressing may be removed from its packaging, and the permeable film release liner is removed and the dressing is secured over the wound except for the portion covered with the pull tab. Accordingly, the permeable film release liner 704 is then removed by pulling a tab 704a which sticks out from under the wound dressing, sliding it out from between the dressing 700 and the skin, and then securing the remaining portion of the adhesive backed bottom layer 702 over and around the wound. For some embodiments, either the permeable film release liner 704 or the top barrier layer 706 should be sufficiently permeable so as to allow the gases in the reservoir (as well as the storage container) to come to equilibrium over an extended period of time during storage in a positively pressurized (preferably) package.

Accordingly, as shown in FIGS. 7A-7E, a tissue dressing 700 according to the present embodiment includes 706 barrier layer holds gas in the gas reservoir 708, which preferably includes a compliant porous insert (not shown) that is an absorbent sponge-like material; perforated or permeable bottom (for example) film/layer 710 which allows minimal restricted gas transfer properties with an adhesive backing, release liner 702 which protects the perimeter adhesive; and permeable film release liner 704 having a pull tab 704a. As shown, preferably, the pull tab for the permeable film release liner is connected to the end of the release liner located opposite the end of the dressing where the pull tab is positioned. This may be accomplished using extra release liner material (as shown in the figures), or by some other means (e.g., natural or synthetic thread and the like).

Other embodiments of the permeable film release liner aspect of the present invention may include a small hole in the permeable film release liner 704 that allows for direct two-way gas transfer between the gas in the reservoir and the gas in the container that the dressing is stored in. The hole size can be optimized based upon the perforated hole pattern in the permeable film such that at least a portion of one hole is always overlapping with any hole in the permeable film. Such embodiments may allow the gases in the reservoir and the storage container (e.g., packaging) to come to equilibrium in pressure or gas concentrations over time, if either the barrier layer 706 or the permeable film release liner 704 are not sufficiently permeable or have permeabilities that are significantly different for the different gases moving into and out of the reservoir.

Still other embodiments of this aspect of the present invention require no adhesive on the portion of the permeable film 710 under the reservoir 708 portion of the dressing. In such embodiments, the design may be modified to make the perimeter release liner 702 narrower inside than the perimeter adhesive such that the permeable film release liner 704 is wide enough to overlap to cover the perimeter adhesive exposed by the perimeter release liner 702.

In other embodiments, the permeable film is protected by covering the pores with a water soluble film (for example) that will disintegrate upon wetting (e.g., upon contact with wound fluid, the film disintegrates). Such an embodiment, thus, need not require a permeable film release liner. Examples of water soluble films that may be used include: starch/cellulose/rice paper type media, polyvinyl alcohol or plga (poly (lactide-co-glycolide) films. Such materials also allow for loading of beneficial agents described in the '630 patent.

Figure 7A:
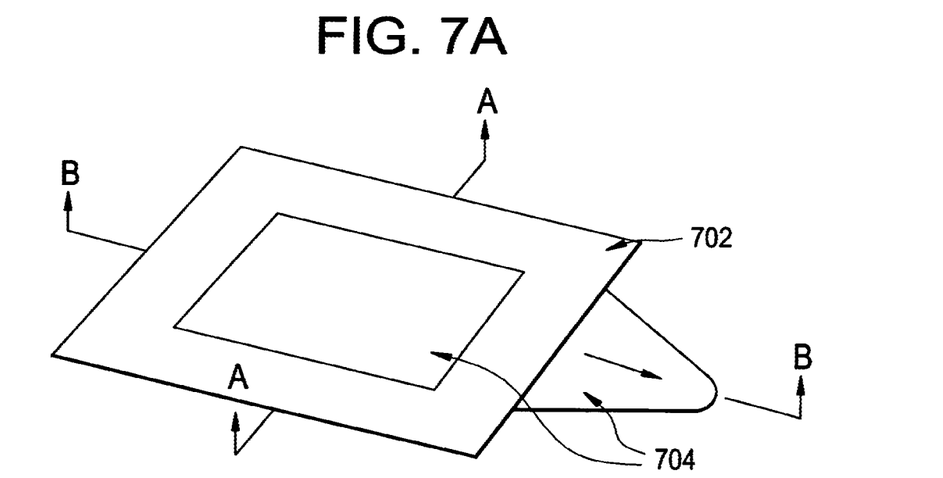
FIG. 7A illustrates a perspective view of a release liner for use with tissue dressings according to some embodiments of the present invention.
Figure 7B:
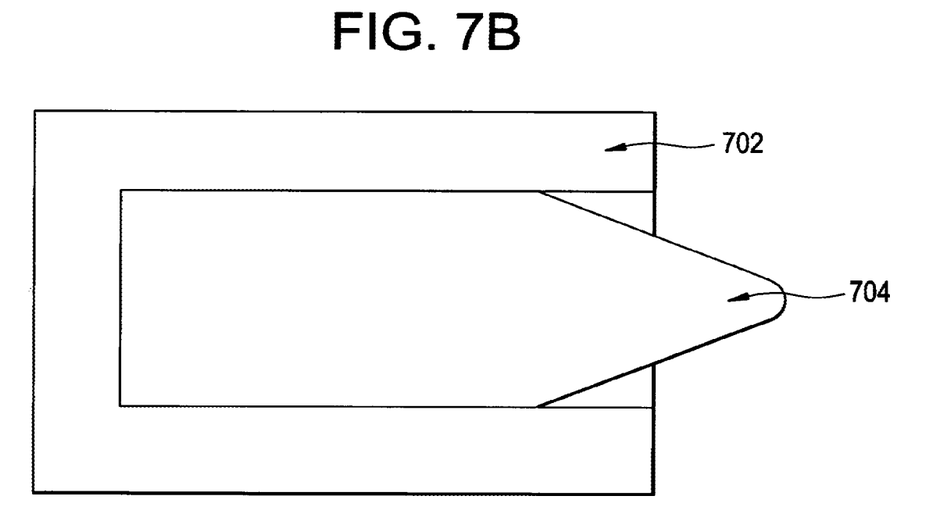
FIG. 7B illustrates a bottom view of a release liner for use with tissue dressings according to some embodiments of the present invention.
Figure 7C:
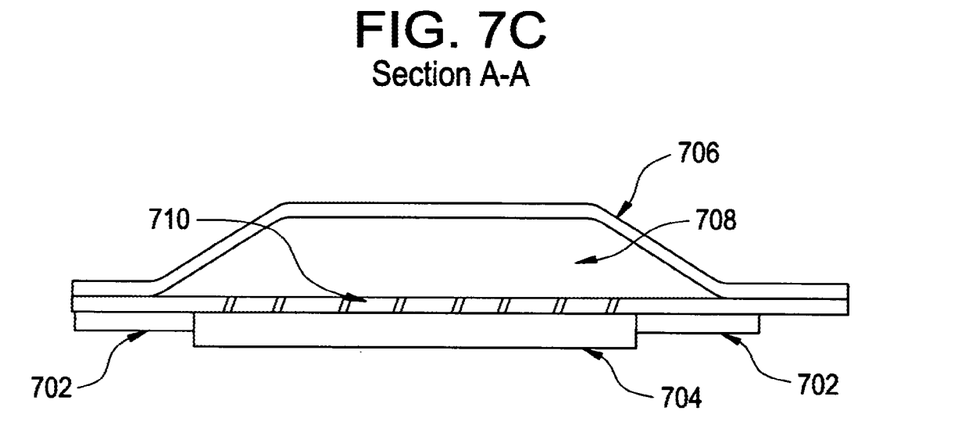
FIG. 7C illustrates a side, cross-sectional view of a tissue dressing having a release liner according to some embodiments of the invention.
Figure 7D:
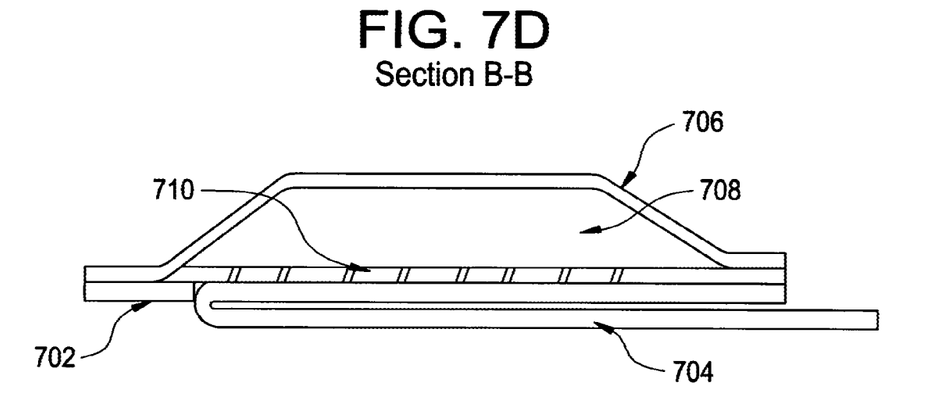
FIG. 7D illustrates a side, cross-sectional view of a tissue dressing having a release liner according to some embodiments of the invention.
Figure 7E:
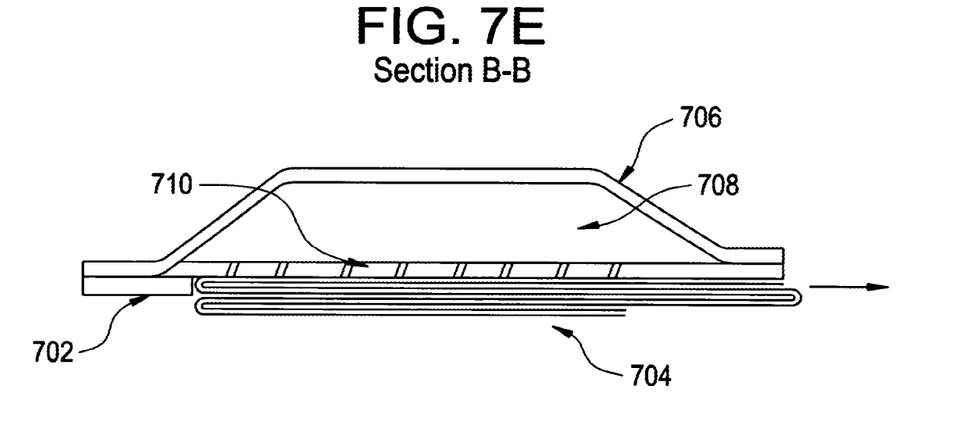
FIG. 7E illustrates a side, cross-sectional view of a tissue dressing having a release liner according to some embodiments of the invention.

In still other embodiments, the permeable film release liner includes folds such that the release liner preferably rolls both off of the dressing and across the wound rather than dragging across the wound surface. It is worth noting that with respect to the illustrated embodiments, gaps and other features are exaggerated to better illustrate the geometry (e.g., the permeable film release liner would lay flat without gas between the layers). Accordingly, in some embodiments, the permeable film release liner may be one layer thick with no folds (FIG. 7C), two layers with a fold opposite the pull direction (with the pull tab protruding from the top or bottom; FIG. 7D), or multiple folds (FIG. 7E). Each design includes particular benefits and may also include certain compromises, depending (for example) on pore size, surface characteristics of the porous surface, adhesive location and type, acceptable gas dilution specs, and wound surface type (for example).

Figure 8A:
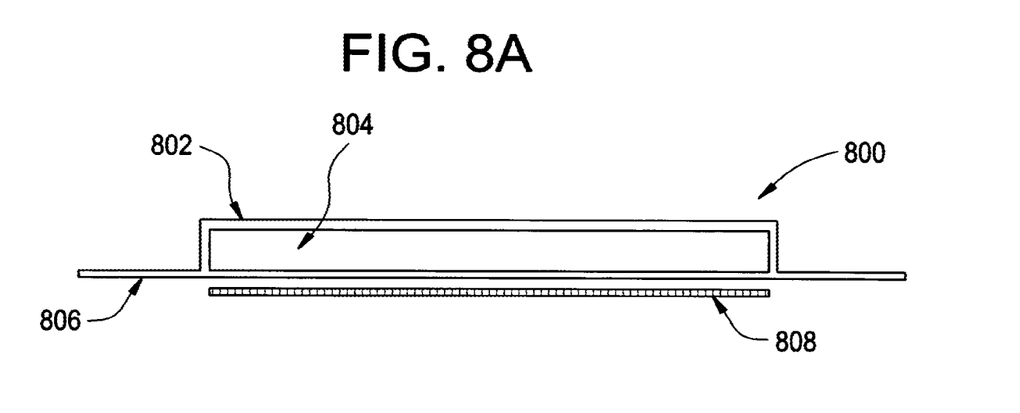
FIG. 8A illustrates a side, cross-sectional view of a tissue dressing having an extended permeable layer according to some embodiments of the invention, and including an absorbent foam on a tissue facing side of the permeable membrane.
Figure 8B:
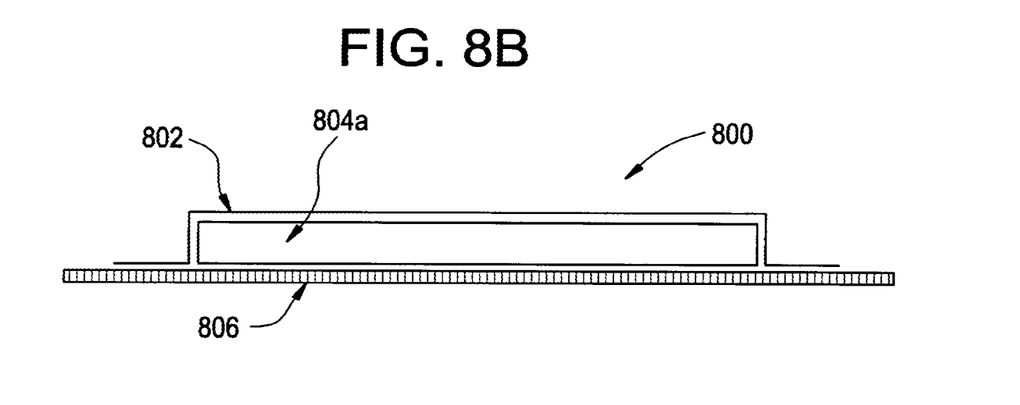
FIG. 8B illustrates a side, cross-sectional view of a tissue dressing having an extended permeable layer according to some embodiments of the invention, and including a porous absorbent material within the reservoir.

In yet other embodiments of the present invention, a tissue dressing device is presented as set out in FIGS. 8A and 8B. As shown, both figures illustrate a tissue dressing 800. In FIG. 8A, the tissue dressing includes a barrier layer 802, a reservoir 804, a permeable membrane (which is sealed with the barrier layer) 806 which extends out beyond the barrier layer either along one portion of the tissue dressing, or preferably extending out along the entire perimeter or substantially the entire perimeter of the dressing. By extending the permeable layer out beyond the edge of the tissue dressing barrier material), the perimeter adhesive and corresponding skin is better able to "breath", gaseous communication, with the environment external to the wound. This enables the adhesive, and thus the tissue dressing, a longer use life. The embodiment shown in FIG. 8A includes an absorbent foam material 808 on the tissue facing side of the permeable layer, while in FIG. 8B, the absorbent foam is provided within the reservoir (not shown).

The foregoing descriptions of specific embodiments of the invention have been presented for purposes of illustration and description. They are not intended to be exhaustive or to limit the invention to the precise embodiments disclosed, and naturally many modifications and variations are possible in light of the above teaching. The embodiments were chosen and described in order to explain the principles of the invention and its practical application, to thereby enable others skilled in the art to best utilize the invention and various embodiments with various modifications as are suited to the particular use contemplated.

The invention claimed is:

1. A wound dressing system for supplying a gas to the wound, comprising:
   a reservoir comprising a flexible top layer not permeable to gas and having a specific size and shape, and a bottom layer permeable to gas and having the same specific size and shape as the top layer, the top and bottom layers sealed together by an adhesive around an entire periphery of the layers, space between the top and bottom layers sealed together comprising a reservoir of a first volume; and
   a package container having a second volume greater than the volume of the reservoir, with the reservoir enclosed in the container;
   the apparatus characterized in that the reservoir is pressurized to a specific pressure above atmospheric pressure with a specic gas, the reservoir is placed in the package container, and the package container is sealed and pressurized with the specific gas to at least the specific pressure.

2. The wound dressing system according to claim 1, wherein the bottom layer of the reservoir has an outside surface and an inside surface, and the outside surface is coated with an adhesive, enabling the reservoir, removed from the packaging container, to be securely applied to the wound.

3. A tissue dressing for maximizing moisture vapor transmission rate (MVTR) comprising:
   a film for covering a target tissue area having sufficient permeability to allow moisture vapor to communicate therethrough;
   a gas reservoir positioned on a side of the film opposite the target tissue area; and
   a hygroscopic dessicant material contained within the reservoir, wherein the desiccant material actively absorbs moisture vapor communicating through the film thereby maximizing MVTR in and around the target tissue area.

4. The tissue dressing according to claim 3, wherein the desiccant material is selected from the group consisting of: polyacrylate powder, fibers and beads, silca gel, Bentonite clay, sodium, potassium, and calcium crystalline hydrated aluminosilicates, synthetic desiccants.

5. The wound dressing system of claim 1 wherein the specific gas is one of oxygen and nitric oxide.

* * * * *